United States Patent [19]

Blandino et al.

[11] Patent Number: 4,958,636

[45] Date of Patent: Sep. 25, 1990

[54] VITAL SIGNS MONITOR PUMPING SYSTEM

[75] Inventors: Thomas Blandino, Madison; Ruth L. Starr, Evansville, both of Wis.

[73] Assignee: Criticare Systems, Inc., Waukesha, Wis.

[21] Appl. No.: 253,712

[22] Filed: Oct. 5, 1988

[51] Int. Cl.$^5$ .............................................. A61B 5/00
[52] U.S. Cl. ...................................... 128/630; 128/177
[58] Field of Search ................................. 128/677–686,
128/672, 664, 719, 901, 630, 774, 76, 648;
417/12, 44, 45, 410, 411, 413, 43, 274, 540, 19,
53; 604/118, 120, 121, 65, 67; 73/272, 706.7

[56] References Cited

U.S. PATENT DOCUMENTS

| | | | |
|---|---|---|---|
| 3,118,383 | 1/1964 | Woodward | 103/53 |
| 3,162,134 | 12/1964 | Lovell | 103/53 |
| 3,221,798 | 12/1965 | Kofink | 158/28 |
| 3,610,782 | 10/1971 | McGuire | 417/326 |
| 3,819,305 | 6/1974 | Klochemann et al. | 417/413 |
| 4,150,922 | 4/1979 | Cuenoud et al. | 417/45 |
| 4,295,471 | 10/1981 | Kaspari | 128/675 |
| 4,493,326 | 1/1985 | Hill et al. | 128/682 |
| 4,669,485 | 6/1987 | Russell | 128/679 |

FOREIGN PATENT DOCUMENTS 0258532 3/1989 European Pat. Off. .

OTHER PUBLICATIONS

"Characterization of the Oscillometric Method for Measuring Indirect Blood Pressure", by L. A. Geddes et al., Biomedical Engineering Center, Purdue University, West Lafayette, Ind., pp. 271-280.

Primary Examiner—Randall L. Green
Assistant Examiner—K. M. Reichle
Attorney, Agent, or Firm—Willian Brinks Olds Hofer Gilson & Lione

[57] ABSTRACT

A pump supplies a variable pressure to an occluding cuff of a blood pressure monitor. This pump includes a pumping member that is driven through a stroke in response to a drive signal having a fixed frequency but a variable duty cycle such that the length of the stroke is variable in response to variations in the duty cycle. The drive signal is generated at a selected driving frequency which is outside of and greater than the measuring frequency range of the blood pressure monitor. In this way, strokes of the pump do not cause pressure variations in the cuff within the measuring frequency range.

21 Claims, 6 Drawing Sheets

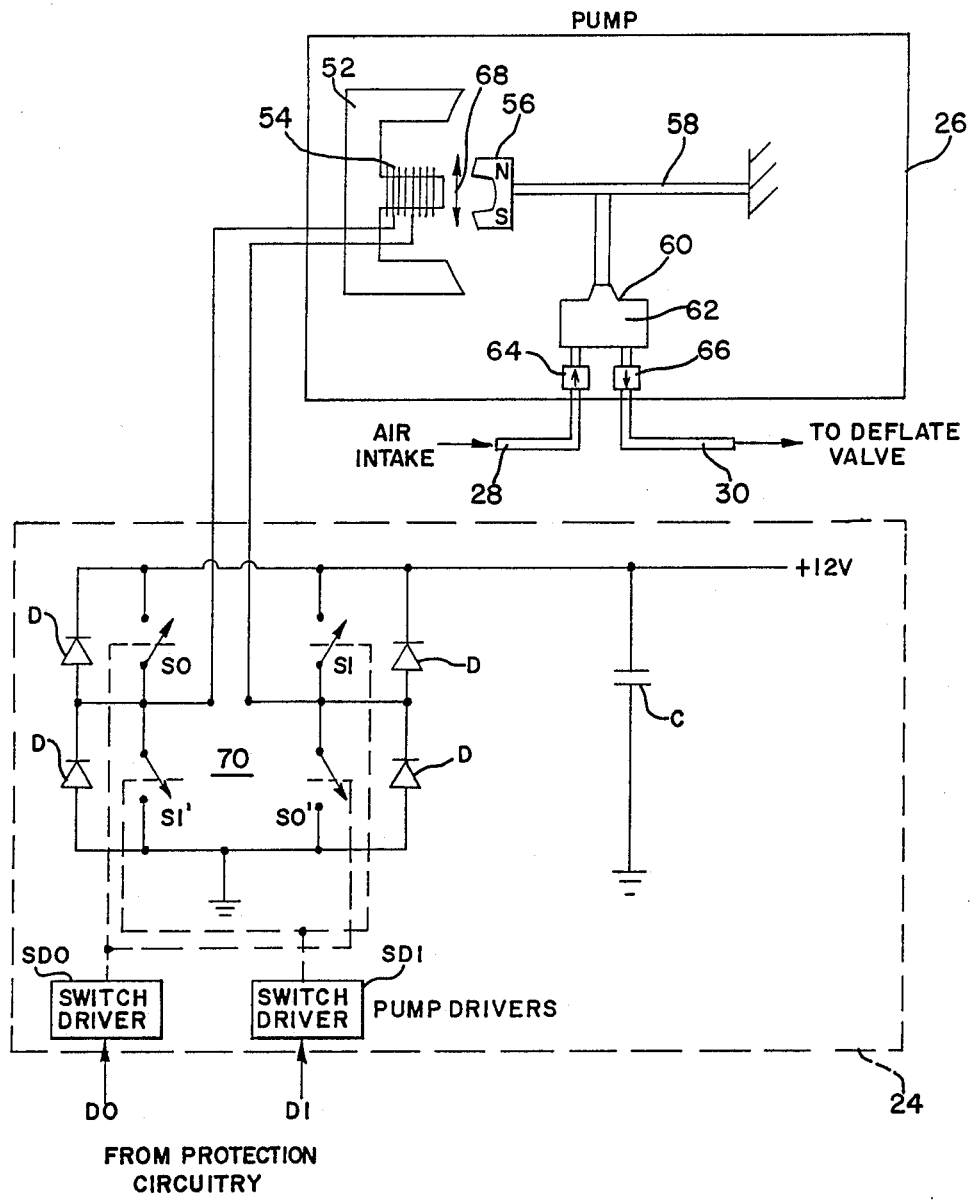
FIG_2

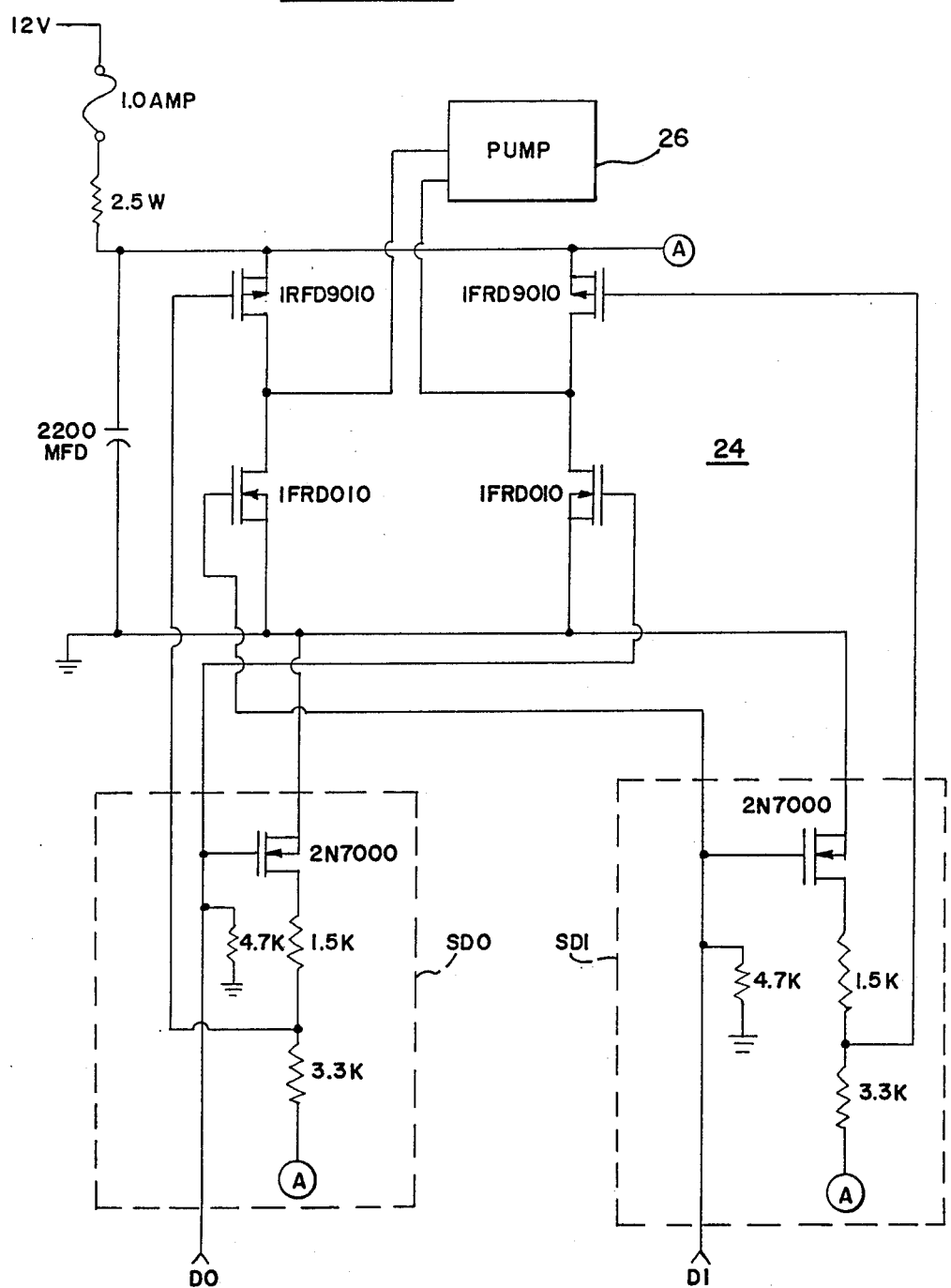
FIG_2a

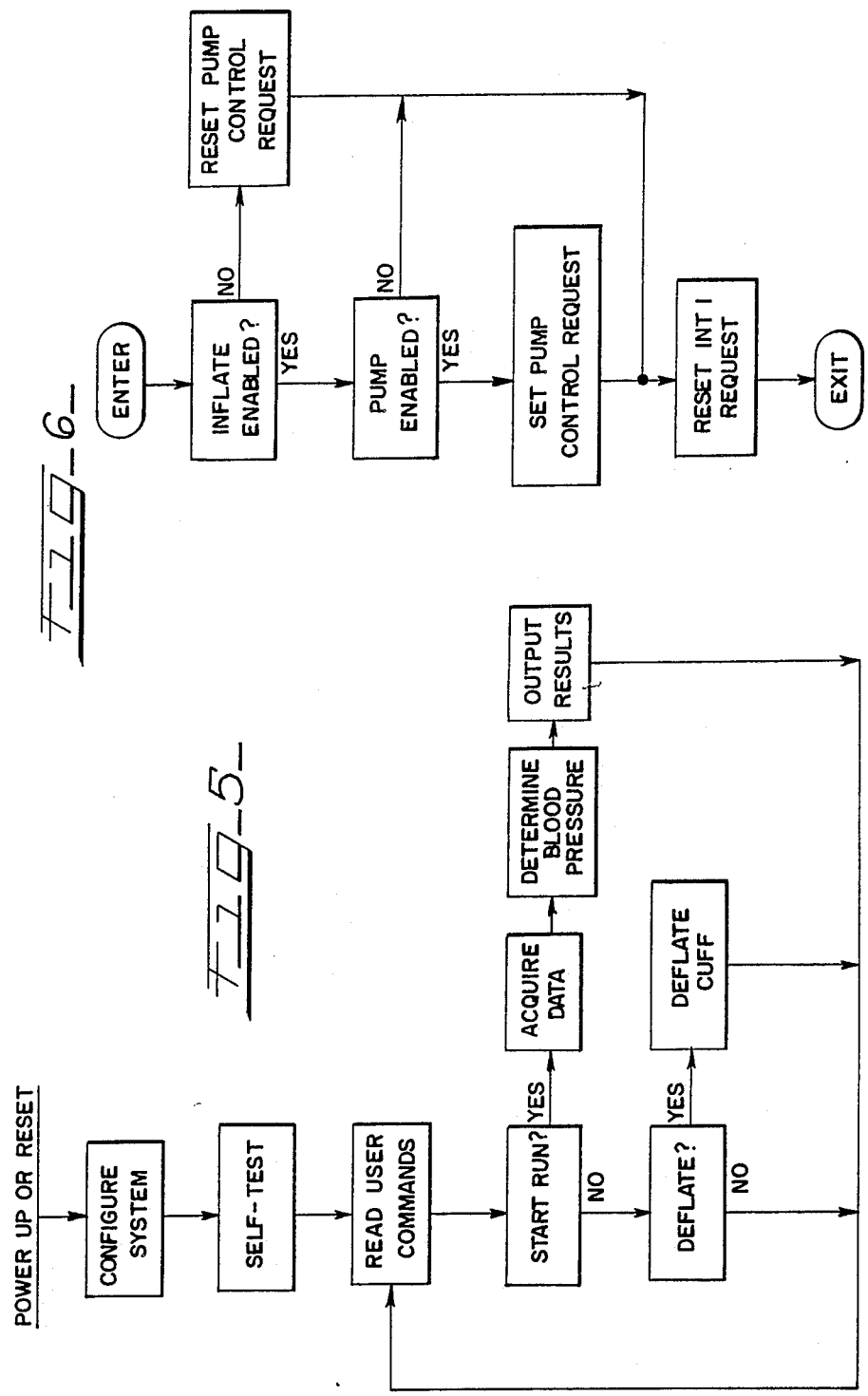

VITAL SIGNS MONITOR PUMPING SYSTEM

BACKGROUND OF THE INVENTION

The present invention relates to a pumping system for a vital signs monitor such as a blood pressure monitor or a gas analyzer.

Vital signs monitors such as blood pressure monitors and gas analyzers require pumps to pressurize a gas or other fluid In a blood pressure monitor the pump pressurizes a blood pressure cuff to occlude blood flow through an extremity of the patient. In a gas analyzer such as a capnometer the pump draws exhaled air from the patient through a sample chamber for analysis, as for example for infrared absorption analysis of exhaled gas concentrations. In both of these examples fluctuations in fluid pressure caused by the pump can interfere with the measurement.

In addition, it is often desirable or necessary to vary the pumping rate of the pump. For example, a capnometer pump is preferably adjustable to control flow rate through the sample cell In a blood pressure monitor the pumping rate is preferably adjustable to obtain the desired rate of change of pressure in the blood pressure cuff.

This invention is directed to an improved pump and pump controller that allow the frequency and pumping rate of the pump to be controlled in a particularly advantageous manner.

There have been a number of prior art pump controllers which supply an oscillating drive signal to a pump in order to control the pumping rate of the pump. Lovell, U.S. Pat. No. 3,162,134, Kofink, U.S. Pat. No. 3,221,798, and McGuire U.S. Pat. No. 3,610,782, all describe pumping systems in which a variable frequency drive signal is provided to a pump. The frequency of the drive signal is adjusted to modify the output rate of the pump as desired. Klochemann, U.S. Pat No. 3,819,305, discloses another type of pumping system which uses individual driving signals at a constant frequency. In Klochemann selected groups of pulses of the driving signal are blocked in order to provide a desired average throughput for the pump. Cuenoud U.S. Pat. No. 4,150,122 describes a micropipetting machine which supplies drive signals to a pump at a fixed frequency. This system counts the total number of pumping cycles in order to deliver the desired volume of liquid.

Woodward, U.S. Pat. No. 3,118,383, describes a pump system which includes a sensor that senses piston position in the pump This sensor automatically cycles the pump when the piston reaches an extreme of travel. In this way, a variable frequency drive signal is provided for the pump.

Of the systems described above, those of Woodward, Lovell Kofink McGuire all operate at variable frequencies. This can create a problem for a vital signs monitor, because pressure fluctuations associated with cycling of the pump can interfere with the vital signs measurement if the fundamental frequency of the pump is allowed to overlap the measuring frequency range of the vital signs monitor. Klochemann and Cuenoud operate pumps at fixed frequencies; however neither is intended for use with a vital signs monitor, and both would exhibit system drawbacks if an attempt were made to adapt them to a vital signs monitor. The approach taken in Klochemann of blocking sets of pulses of the drive signal to obtain an average pump throughput can result in excessive pressure variations. The Cuenoud micropipetter counts cycles to provide a desired dispensed volume, and is not well-suited to maintain a desired pressure.

The present invention is directed to an improved pumping system for a vital signs monitor that allows the pumping rate to be adjusted simply and reliably, that allows the pump to be operated at a fixed frequency well above the frequency range in which the measurement is made, and that allows the pumping rate to be controlled by varying the duty cycle of the drive signal while maintaining the fundamental frequency of the pump at a predetermined value.

SUMMARY OF THE INVENTION

This invention is a component system for a vital signs monitor of the type that comprises a measuring chamber and means for measuring a parameter of a fluid contained in the measuring chamber in a measuring frequency range, wherein the parameter varies as a function of fluid pressure and is indicative of a vital sign of the patient.

According to a first feature of this invention, a vital signs monitor of this type is provided with a variable pumping rate pump connected to the measuring chamber to control pressure in the measuring chamber. This pump comprises a pumping member mounted to oscillate and an electromagnet coupled to the pumping member to drive the pumping member through a stroke in response to a drive signal. The drive signal is generated at a fixed frequency and with a variable energy per cycle, i.e., variable duty cycle or amplitude. This drive signal is applied to the electromagnet and the energy per cycle of the drive signal affects the length of the stroke and therefore the pumping rate of the pump. With this arrangement the pumping rate of the pump can readily be adjusted as desired without modifying the fundamental frequency of the pump and therefore the fundamental frequency of pressure fluctuations in the measuring chamber associated with pump cycling.

According to a second feature of this invention, a vital signs monitor includes a variable pumping rate pump connected to the measuring chamber to control pressure in the measuring chamber. This pump comprises a pumping member and means for driving the pumping member through a stroke in response to a drive signal which has at least one variable drive parameter, wherein the pumping rate of the pump varies as a function of the variable drive parameter. The drive signal is periodically generated with a selected driving frequency which is outside of and greater than the measuring frequency range to prevent the strokes of the pump from causing pressure variations in the measuring chamber in the measuring frequency range.

In the embodiment described below the vital signs monitor is a blood pressure monitor and the measuring chamber is a blood pressure cuff. By ensuring that the driving frequency is greater than the measuring frequency range, pressure fluctuations associated with cycling of the pump do not interfere with pressure measurements used to determine blood pressure of the patient.

The invention itself, together with further objects and attendant advantages, will best be understood by reference to the following detailed description, taken in conjunction with the accompanying drawings.

BRIEF DESCRIPTION OF THE DRAWINGS

FIG. 2 is a more detailed schematic diagram of the pump and pump driver circuitry of the embodiment of FIG. 1.

FIG. 2a is a detailed schematic diagram of the pump driver of FIG. 2.

FIG. 5 is a flow chart of a background, non-interrupt program executed by the microcomputer of FIG. 1.

FIG. 6 is a flow chart of a foreground, interrupt driven routine executed by the microcomputer of FIG. 1.

DETAILED DESCRIPTION OF THE PRESENTLY PREFERRED EMBODIMENTS

Figure 1:
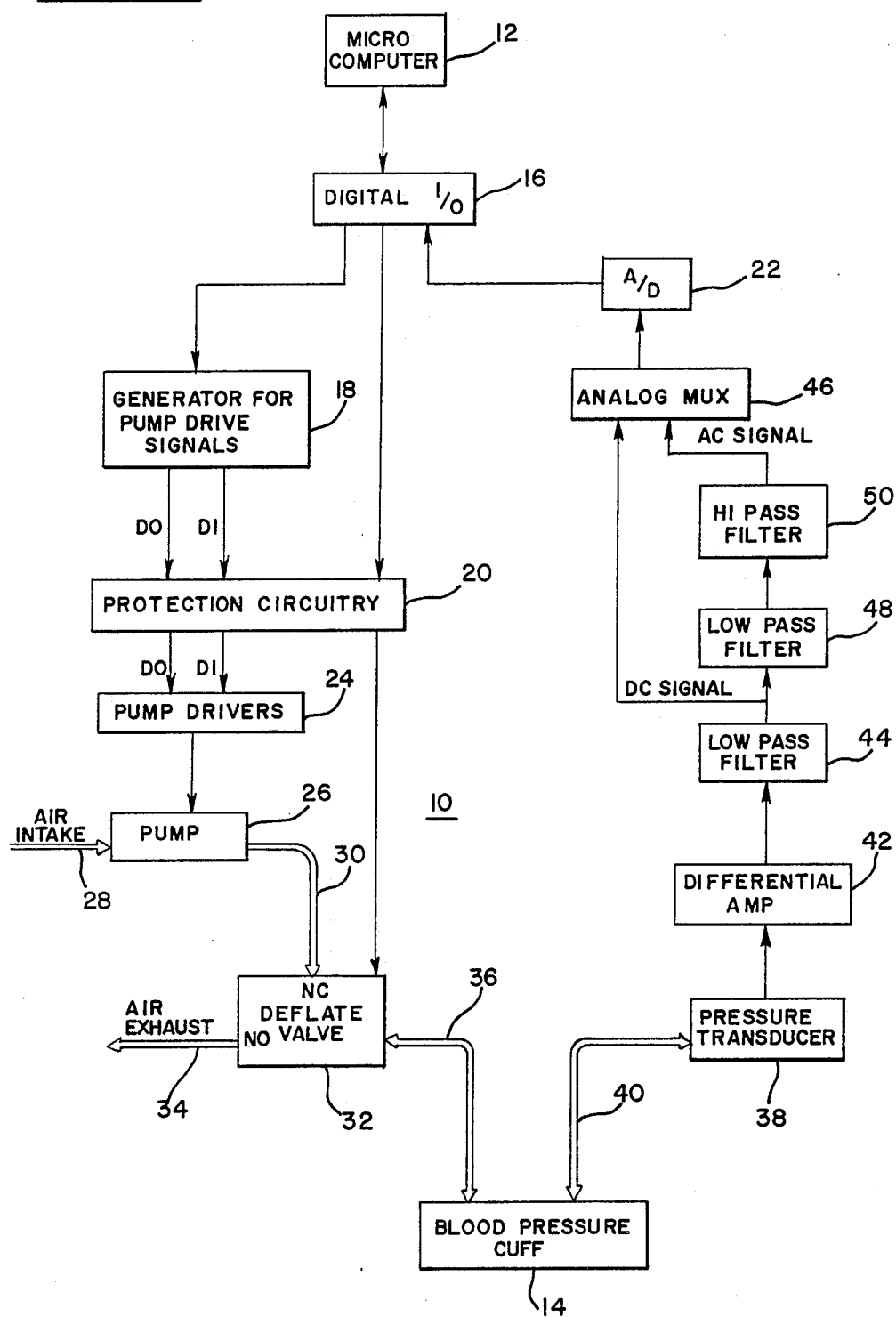
FIG. 1 is a block diagram of a blood pressure monitor that incorporates a presently preferred embodiment of this invention.

Turning now to the drawings, FIG. 1 shows a block diagram of a blood pressure monitor 10 that incorporates a presently preferred embodiment of the pumping system of this invention. This blood pressure monitor 10 includes microcomputer 12 that controls the air pressure supplied to a blood pressure cuff 14 and monitors pressures within the cuff 14 in order to determine the mean, systolic, and diastolic blood pressures of a patient.

As shown in FIG. 1, the microcomputer 12 is interfaced by a digital I/O circuit 16 with a generator for pump drive signals 18, protection circuitry 20 and an A to D converter 22. The operation of the generator 18 will be described in greater detail below in conjunction with FIG. 3. Here, it is enough to state that the generator 18 generates two pump drive signals D0, D1 which are of fixed frequency and which have a variable duty cycle. The pump drive signals D0, D1 are supplied to the protection circuitry 20. During normal operation the protection circuitry 20 merely passes the pump drive signals D0, D1 to pump drivers 24 which convert the logic level signals D0, D1 to power level drive signals and apply them to a pump 26. The pump 26 draws air from an air intake 28 and supplies it under pressure to a conduit 30 that interconnects the pump 26 with a deflate valve 32. The deflate valve 32 is controlled by the microcomputer 12 and normally prevents air in the conduit 30 from reaching the cuff 14. However, when the microcomputer 12 operates to pressurize the blood pressure cuff 14, the microcomputer 12 controls the deflate valve 32 to pass pressurized air from the conduit 30 to the blood pressure cuff 14 via a conduit 36.

The blood pressure cuff 14 is a conventional occluding cuff intended to be wrapped around an extremity such as an upper arm of a patient. The blood pressure cuff 14 occludes blood flow past the cuff when it is inflated to a sufficiently high pressure, in the conventional manner.

The pressure of the cuff 14 is also determined in part by the blood pressure of the patient. A pressure transducer 38 is connected to the cuff 14 via a conduit 40, and the transducer 38 generates an output signal that is indicative of the pressure within the cuff 14 and is applied to a differential amplifier 42. The amplified output signal is first filtered in a low pass filter 44, and the output of this low pass filter 44 is a DC signal indicative of the DC pressure within the cuff 14. The DC signal is applied to the A to D converter 22 via an analog multiplexer 46.

The output of the low pass filter 44 is also applied to a second low pass filter 48 and then to a high pass filter 50. The output of this high pass filter 50 is an AC signal indicative of pressure fluctuations in the cuff 14 associated with individual pulses of the patient This AC signal is also applied to the A to D converter 22 via the multiplexer 46.

In use, the microcomputer 12 controls the pump 26 and the valve 32 to provide a smoothly increasing pressure to the cuff 14. The microcomputer 12 monitors the AC signal from the high pass filter 50 and the DC signal from the low pass filter 44 in order to determine the peak amplitude pulses in the AC signal and the associated DC signals. Then, mean, systolic, and diastolic blood pressures of the patient are determined using standard oscillometric techniques as described for example in the paper "Characterization of the Oscillometric Method for Measuring Indirect Blood Pressure", L.A. Geddes et al., *Annals of Biomedical Engineering*, Volume 10, pages 271-280 (1982), and European Patent Application 0 258 532.

As explained above, the present invention is directed to an improved pumping system, and for this reason the protection circuitry 20, the microcomputer 12, and the elements 38-50 will not be described in greater detail here. These elements have only been discussed above to provide a better understanding of the environment in which this embodiment operates. This embodiment will be understood more clearly with reference to FIGS. 2-7 as described below.

As shown in FIG. 2, the pump 26 includes an electromagnet 52 that in turn includes a coil 54. The electromagnet 52 is magnetically coupled with a permanent magnet 56 that is mounted for oscillation on a spring member 58. The spring member 58 is coupled to a pumping member 60, that can be a diaphragm as shown schematically in FIG. 2, a pump piston, or the like. The pumping member 60 defines one surface of a pumping chamber 62 that is in fluid communication with the intake 28 and the conduit 30 via respective check valves 64, 66.

In operation, current through the coil 54 alternates in direction. When the current is flowing in a first direction the magnet 56 is pulled upwardly along the direction shown by the arrow 68, thereby raising the pumping member 60. When current is flowing in the opposite direction the magnet 56 is moved downwardly along the direction of the arrow 68, thereby moving the pumping member 60 downwardly. In this way, the pumping member 60 is oscillated and the pump 26 draws air through the air intake 28 and supplies pressurized air to the deflate valve 32 via the conduit 30.

As shown in FIG. 2, current to the coil 54 is controlled via an H bridge 70 that includes four switches S0, S0', S1, S1'. The switches S0, S0' are controlled by a switch driver SD0, and the switches S1, S1' are controlled by a switch driver SD1. The switch drivers SD0, SD1 are in turn controlled by the pump drive signals D0, D1. When the pump drive signal D0 is in the on state, the switch driver SD0 closes the two switches S0, S0', thereby applying 12 volts across the coil 54 with a first polarity. When the pump drive signal D0 is in the off state, the switch driver SD0 opens the switches S0, S0' to prevent current from flowing through the coil 54. The pump drive signal D1 controls the switch driver SD1 to operate the switches S1, S1' in a similar manner to pass current of reverse direction through the coil 54. The diodes D rectify currents generated when the switches S0, S0', S1, S1' are opened for storage in the capacitor C, thereby improving efficiency of operation The coil 54 of the pump 26 generates a large back EMF when current through the coil 54 collapses. The diodes D return much of the electrical energy in this back EMF to the supply, thereby increasing battery life when the supply is battery powered.

Figure 3:
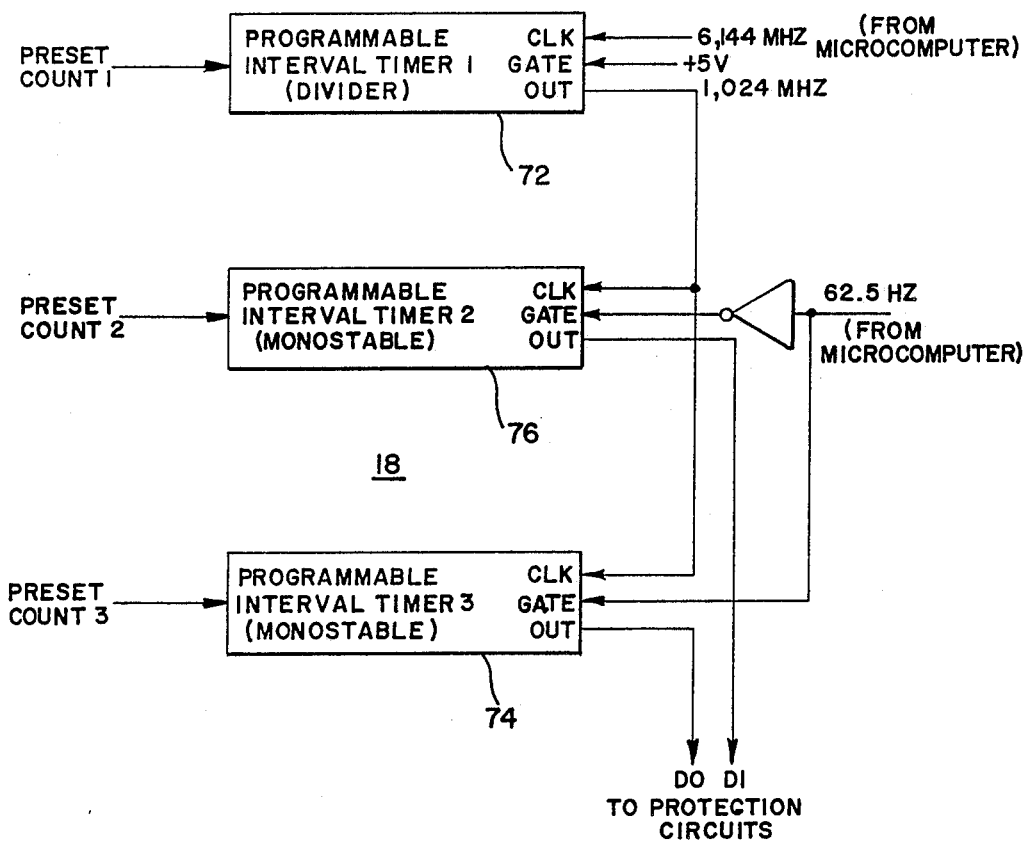
FIG. 3 is a more detailed block diagram of the generator for pump drive signals of FIG. 1.
Figure 4:
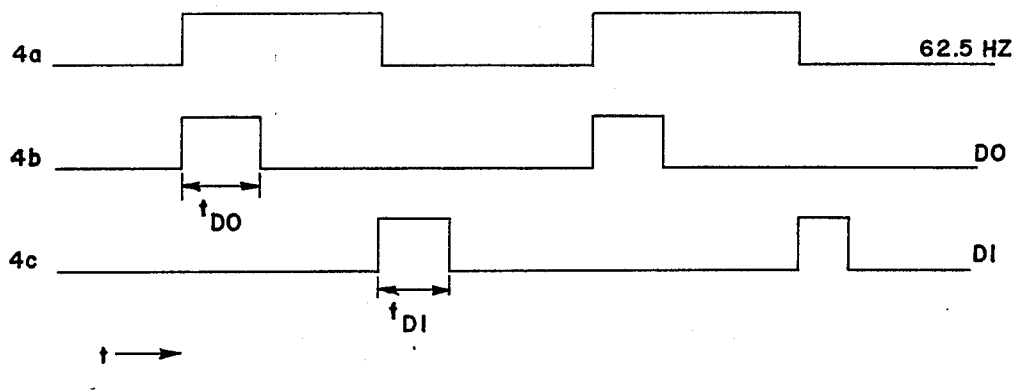
FIGS. 4a-4c are wave form diagrams of the generator of FIG. 3.

FIG. 3 provides further details of the generator for pump drive signals 18. As shown in FIG. 3, this generator 18 includes three programmable interval timers 72, 74, 76. Each of the timers 72, 74, 76 operates only when a logic high signal is applied to its respective gate Each operates to count clock signals on its respective clock input and to supply an output signal on its respective output until the count of the clock signals reaches a preset count supplied by the microcomputer 12. The timer 72 receives a clock signal of 6.144 MHZ from the microcomputer 12, is gated on continuously, and is provided with a preset count such that the output signal has a frequency of 1.024 MHZ. This 1.024 MHZ signal is applied as a clock to the two remaining timers 74, 76. These two timers 74, 76 are gated with inverse polarity by a gating signal of 62.5 HZ from the microcomputer. This gating signal is applied directly to the gate of the timer 74 and is applied with inverted polarity to the gate of the timer 76. This arrangement ensures that only one of the timers 74, 76 is counting at any given time The two timers 74, 76 are provided with identical preset counts by the microcomputer 12, and these preset counts determine the duration of the output signals D0, D1 generated by the timers 74, 76. These output signals are the pump drive signals D0, D1 described above. Each of the output signals D0, D1 is in the logic high state for the time interval required to count from zero to the respective preset count, in cycles of the clock signal.

FIGS. 4a-4c are waveform diagrams that explain in greater detail the operation of the generator of FIG. 3. FIG. 4a shows the 62.5 HZ gating signal that is applied to the gates of the timers 74, 76. FIG. 4b shows the pump drive signal D0 generated by the timer 74. Because the timer 74 is only gated on during the first half of each cycle of the 62.5 HZ gating signal, the pump drive signal D0 goes on with the rising edge of the 62.5 HZ gating signal. The pump drive signal D0 stays on for a time $t_{D0}$ which is directly proportional to the preset count. As shown in FIG. 4c the pump drive signal D1 goes on at the falling edge of the 62.5 HZ gating signal, and the pump drive signal D1 stays on for a time $t_{D1}$ directly proportional to the preset count.

It should be noted that because the 62.5 HZ gating signal is maintained at a fixed frequency, the pump drive signals D0, D1 are each generated at a fixed frequency. In this case 62.5 HZ (the frequency of the pump drive signals D0, D1) was chosen equal to the resonant frequency of the spring member 58, magnet 56, and pumping member 60 when the pump 26 was operating against a significant back pressure (100 mm Hg in this case). In this way the pump 26 is operated at maximum efficiency, and the fundamental frequency of noise associated with cycling of the pump 26 is maintained at a constant 62.5 HZ. The microcomputer varies the preset counts for the timers 74, 76 as described below to vary $t_{D0}$ and $t_{D1}$, and therefore the duty cycles of the pump drive signals D0, D1. In general, a higher duty cycle results in a larger excursion for the magnet 56 and therefore a longer stroke for the pumping member 60 and a higher output for the pump 26 The microcomputer controls the duty cycles of the pump drive signals D0, D1 to achieve the desired pumping rate of the pump 26, as shown in FIGS. 5-7.

FIG. 5 shows a flow chart that outlines the general operation of the blood pressure monitor 10. Generally speaking, when commanded to initiate a measurement, the microcomputer gradually increases the duty cycle of the pump drive signals D0, D1 to increase pressure in the cuff 14. As pressure is being increased, the microcomputer monitors pressure pulses in the cuff 14 and from these pulses and the known DC pressure in the cuff 14 determines the blood pressure and outputs the results. At the end of the measurement, the microcomputer 12 deflates the cuff 14 and awaits further commands.

FIG. 6 shows a foreground, interrupt driven routine that resets a Pump Control Request flag in the event the inflation cycle is disabled and sets the Pump Control Request flag in the event the inflation cycle is enabled and the pump is enabled. The routine of FIG. 7 is executed once per cycle of the pump, i.e., at a frequency of 62.5 HZ.

Figure 7:
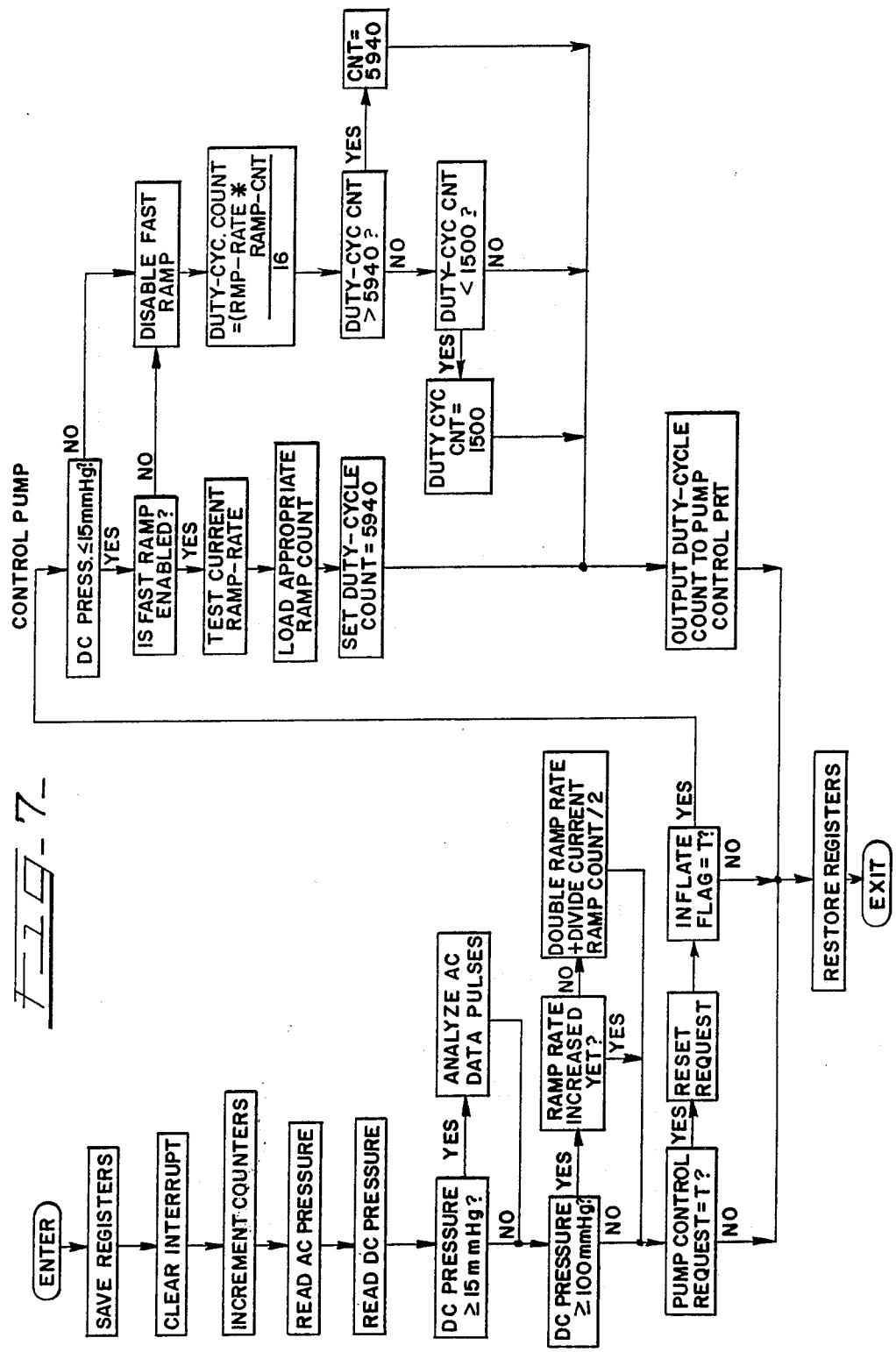
FIG. 7 is a flow chart of a foreground, interrupt driven routine executed by the microcomputer of FIG. 1.

FIG. 7 shows a flow chart of an interrupt driven program that determines the duty cycles of the pump drive signals D0, D1. The program of FIG. 7 is executed once every 4 milliseconds on an interrupt driven basis.

The routine of FIG. 7 begins by saving appropriate registers, clearing the interrupt, and incrementing counters The main counter important for this discussion that is incremented is the Ramp Count which is incremented by one every 4 milliseconds. The program then reads the AC and DC pressures from the A to D converter 22 and analyzes the AC pressure signals for pulses in the event the DC pressure is greater than or equal to 15 mm Hg.

The routine then checks to determine whether DC pressure is greater than or equal to 100 mm Hg. When this condition is first detected, the variable Ramp Rate is doubled, and the variable Ramp Count is divided by 2. This is done to maintain the rate of pressure increase in the cuff 14 more nearly constant during the inflation cycle.

The routine then examines the Pump Control Request flag, that is set with a frequency of 62.5 HZ by the routine of FIG. 6 described above If the Pump Control Request flag is set, it is then reset and the Inflate flag is examined Assuming the Inflate flag is set (indicating that an inflation cycle is in progress) the routine then checks to determine whether DC pressure is less than or equal to 15 mm Hg. If so, the routine checks to see if the fast ramp feature is enabled. If so, the routine loads an appropriate Ramp Count for the current Ramp Rate and sets the Duty Cycle Count equal to 5940. The Duty Cycle Count is then supplied as the preset counts to the timers 74, 76 of FIG. 3. This branch of the routine ensures that the pump 26 is operated at a maximum pumping rate early in the inflation cycle when the DC pressure is less than 15 mm Hg. A Duty Cycle Count of 5940 results in $t_{D0}$ and $t_{D1}$ equal to $5940 \times 1.024 \times 10^{-6}$ seconds, or a little over 6 milliseconds.

If the DC pressure is greater than or equal to 15 mm Hg, or if the fast ramp is disabled, the routine sets the Duty Cycle Count equal to the Ramp Rate multiplied by the Ramp Count divided by 16. In this embodiment the Ramp Rate is equal to 5 for pressures less than 100 mm Hg and to 10 for pressures greater than or equal to 100 mm Hg. The Duty Cycle Count is then clamped between a minimum value of 1500 and a maximum value of 5940, and is supplied to the timers 74, 76 as described above.

The following details are provided by way of illustration only to define the illustrated embodiment in greater detail. The pump 26 can be a conventional design such as that sold by Binaca Products, Inc. of Bordentown, N.J. as Model No. BP-101, supplied with a 12 volt coil (500 windings of #26 gauge wire). The pump driver of FIG. 2 can be constructed as shown in detail in FIG. 2a, in which the diodes D are not shown separately because they are included in the FET's. The three timers 72, 74, 76 can be implemented using a type 82C54 presettable counter.

Of course, many alternatives are possible. For example, the full bridge circuit of FIG. 2a can be implemented using four N-channel FET's. In addition half bridge and push-pull circuits may be used in place of the full bridge circuit of FIG. 2a.

From the foregoing description it should be apparent that the microprocessor controls the duty cycle of the pump drive signals D0, D1 in order to control the stroke and therefore the pumping rate of the pump 26, while maintaining the fundamental frequency of operation of the pump 26 at a constant 62.5 HZ. This approach provides particular advantages in that the pump frequency is kept constant while the pumping rate is varied, with a minimum of resistive losses in the pump driver. One alternative approach which suffers from the disadvantage of increased resistive losses is that the pump driving signals may be generated at a fixed duty cycle and a fixed frequency bu at a variable amplitude in order to vary the energy per cycle of the pump drive signals and therefore the stroke and pumping rate of the pump 26.

In the blood pressure monitor 10, the measuring frequency range that is relevant for the blood pressure measurement is the range from 0–12 HZ. Higher frequency measurements are not significant in view of physiologically relevant pulse rates. The filters 50, 48, 44 ensure that the signals monitored by the microcomputer 12 are in the frequency range of 0–12 HZ. An important feature of this invention is that the pump 26 operates at a pumping frequency that is significantly above the measuring frequency range, throughout the full range of pumping rates of the pump 26. In the embodiment described above, the fundamental frequency of pressure fluctuations associated with the pump 26 is at 62.5 HZ, well above and completely outside of the measuring frequency range of 0–12 HZ. In this way, measurement artifacts associated with pump cycling are substantially eliminated in a low cost, efficient and reliable manner.

Of course, it should be understood that a wide range of changes and modifications can be made to the preferred embodiment described above. For example, this invention is not limited to use with blood pressure monitors, but can also be used with other vital signs monitors such as gas analyzers for measuring concentrations of selected gases in the exhaled air of a patient. Also, analog circuitry can be used instead of the digital system discussed above to adjust the duty cycle or the amplitude of the drive signal. It is therefore intended that the foregoing detailed description be regarded as illustrative rather than limiting, and that it be understood that it is the following claims, including all equivalents, which are intended to define the scope of this invention.

We claim:

1. In a vital signals monitor of the type comprising a measuring chamber and means for measuring a parameter of a fluid contained in the measuring chamber, wherein the parameter varies as a function of fluid pressure and is indicative of a vital sign of a patient, a system for controlling fluid pressure in the chamber comprising:

a variable pumping rate pump connected to the measuring chamber to control pressure in the measuring chamber, said pump comprising a pumping member mounted to oscillate through a stroke and operative to pump fluid into the measuring chamber in response to oscillation of the pumping member, and an electromagnet coupled to the pumping member to drive the pumping member through the stroke in response to a drive signal;

a drive signal generator which generates the drive signal for the pump at a fixed frequency and a variable energy per cycle of the drive signal, wherein the drive signal is applied to the electromagnet and the energy per cycle of the drive signal affects the length of the stroke and therefore the pumping rate of the pump.

2. The invention of claim 1 wherein the pumping member oscillates at a resonant frequency against a selected fluid back pressure, and wherein the fixed frequency of the drive signal is equal to the resonant frequency.

3. The invention of claim 1 wherein the measuring chamber comprises a blood pressure cuff and wherein the parameter is a pressure parameter of fluid in the blood pressure cuff.

4. The invention of claim 1 wherein the drive signal generator generates the drive signal with a fixed frequency and a variable duty cycle.

5. The invention of claim 4 wherein the drive signal generator generates the drive signal with a fixed amplitude.

6. The invention of claim 1 wherein the measuring means measures the parameter in a selected measuring frequency range, and wherein the fixed frequency is above and outside of the selected measuring frequency range.

7. The invention of claim 1 wherein the drive signal generator is powered by a voltage supply, wherein the electromagnet generates a back EMF, and wherein the drive signal generator comprises means for returning electrical energy associated with the back EMF generated by the electromagnet to the voltage supply.

8. The invention of claim 7 wherein the voltage supply comprises a capacitor and wherein the returning means comprises at least one rectifier connected between the electromagnet and the capacitor to direct electrical current associated with the back EMF to the capacitor.

9. In a vital signs monitor of the type that comprises a measuring chamber and means for measuring a parameter, having a frequency within a measuring frequency range, of a fluid contained in the measuring chamber, wherein the parameter varies as a function of fluid pressure and is indicative of a vital sign of a patient, a system for controlling fluid pressure in the measuring chamber comprising:

a variable pumping rate pump connected to the measuring chamber to control pressure in the measuring chamber, said pump comprising a pumping member and means for driving the pumping member through a stroke in response to a drive signal which has at least one variable drive parameter, wherein the pumping rate of the pump varies as a function of the variable drive parameter;

control means for periodically generating the drive signal with a selected driving frequency to cause the pump to pump at a selected pumping rate, said driving frequency being outside of and greater than the measuring frequency range to prevent the strokes of the pump from causing pressure variations in the measuring chamber in the measuring frequency range.

10. The invention of claim 9 wherein the variable drive parameter is duty cycle.

11. The invention of claim 10 wherein the selected driving frequency is fixed.

12. The invention of claim 11 wherein the vital signs monitor comprises a blood pressure monitor and wherein the measuring chamber comprises an occluding cuff.

13. The invention of claim 11 wherein the drive signal has a fixed amplitude.

14. The invention of claim 9 wherein the control means is powered by a voltage supply, wherein the pump driving means generates a back EMF, and wherein the control means comprises means for returning electrical energy associated with the back EMF generated by the pump driving means to the voltage supply.

15. The invention of claim 14 wherein the voltage supply comprises a capacitor, and wherein the returning means comprises at least one rectifier connected between the pump drive means and the capacitor to direct electrical current associated with the back EMF to the capacitor.

16. In a blood pressure monitor of the type that includes an occluding cuff and means for monitoring pressure variations in the cuff in a measuring frequency range to determine a blood pressure parameter of a patient, a system for supplying a smoothly increasing pressure to the cuff comprising:

a variable pumping rate pump connected to the cuff to inflate the cuff, said pump comprising a pumping member and means for driving the pumping member through a stroke in response to a drive signal which has at least one variable parameter, wherein the pumping rate of the pump varies as a function of the variable parameter;

control means for periodically generating the drive signal with a selected driving frequency such that the variable parameter is varied over time to cause the pump to gradually increase the pressure in the cuff, said selected driving frequency being outside of and greater than the measuring frequency range to prevent the strokes of the pump from causing pressure variations in the cuff in the measuring frequency range.

17. The invention of claim 16 wherein the variable drive parameter is duty cycle.

18. The invention of claim 17 wherein the selected driving frequency is fixed.

19. The invention of claim 18 wherein the drive signal has a fixed amplitude.

20. The invention of claim 16 wherein the control means is powered by a voltage supply, and wherein the control means comprises means for returning electrical energy associated with a back EMF generated by the pump driving means to the voltage supply.

21. The invention of claim 20 wherein the voltage supply comprises a capacitor, and wherein the returning means comprises at least one rectifier connected between the pump driving means and the capacitor to direct electrical current associated with the back EMF to the capacitor.

* * * * *

UNITED STATES PATENT AND TRADEMARK OFFICE
CERTIFICATE OF CORRECTION

PATENT NO. : 4,958,636

DATED : September 25, 1990

INVENTOR(S) : Thomas Blandino et al.

It is certified that error appears in the above-identified patent and that said Letters Patent is hereby corrected as shown below:

In column 1, line 10, after "fluid" please insert --.--.

In column 1, line 22, after "cell" please insert --.--.

In column 1, line 51, after "pump" please insert --.--.

In column 1, line 56, after "Lovell" please insert --,--; and after "Kofink" please insert --,--.

In column 3, line 51, after the first occurrence of "32" please insert --.--.

In column 4, line 10, after the first occurrence of "50" please insert --.--.

In column 4, line 12, after "patient" please insert --.--.

In column 5, line 9, after "operation" please insert --.--.

In column 5, line 19, after "gate" please insert --.--.

In column 5, line 34, after "time" please insert --.--.

UNITED STATES PATENT AND TRADEMARK OFFICE
CERTIFICATE OF CORRECTION

PATENT NO. : 4,958,636
DATED : September 25, 1990
INVENTOR(S) : Thomas Blandino et al.

It is certified that error appears in the above-identified patent and that said Letters Patent is hereby corrected as shown below:

In column 6, line 6, after "26" please insert --.--.
In column 6, line 37, after "counters" please insert --.--.
In column 6, line 53, after "above" please insert --.--.
In column 6, line 55, after "examined" please insert --.--.
In column 7, line 39, please delete "bu" and substitute therefor --but--.

Column 8:
In claim 1, line 1, please delete "signals" and substitute therefor --signs--.

Signed and Sealed this

Twenty-seventh Day of October, 1992

*Attest:*

DOUGLAS B. COMER

*Attesting Officer*      *Acting Commissioner of Patents and Trademarks*